(12) United States Patent
Martinez et al.

(10) Patent No.: US 11,160,735 B1
(45) Date of Patent: Nov. 2, 2021

(54) LONG WEAR LIP COSMETIC SYSTEM AND TOPCOAT

(71) Applicant: L'OREAL, Paris (FR)

(72) Inventors: Santana Nicole Martinez, Howell, NJ (US); Nadin Ahmed Gomez, Monroe, NJ (US); Purvesh Patel, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/910,729

(22) Filed: Jun. 24, 2020

(51) Int. Cl.
*A61Q 1/04* (2006.01)
*A61K 8/03* (2006.01)
*A61Q 1/06* (2006.01)
*A61K 8/891* (2006.01)

(52) U.S. Cl.
CPC ............... *A61K 8/03* (2013.01); *A61K 8/891* (2013.01); *A61Q 1/06* (2013.01)

(58) Field of Classification Search
None
See application file for complete search history.

(56) References Cited

U.S. PATENT DOCUMENTS

| | | | |
|---|---|---|---|
| 5,505,937 A | 4/1996 | Castrogiovanni et al. | |
| 5,874,069 A | 2/1999 | Mendolia et al. | |
| 5,911,974 A | 6/1999 | Brieva et al. | |
| 5,919,441 A | 7/1999 | Mendolia et al. | |
| 5,965,112 A | 10/1999 | Brieva et al. | |
| 5,981,680 A | 11/1999 | Petroff et al. | |
| 5,985,298 A | 11/1999 | Brieva et al. | |
| 6,051,216 A | 4/2000 | Barr et al. | |
| 6,074,654 A | 6/2000 | Drechsler et al. | |
| 6,139,823 A | 10/2000 | Drechsler et al. | |
| 6,780,422 B2 | 8/2004 | Brieva et al. | |
| 6,908,621 B2 | 6/2005 | Jose et al. | |
| 7,871,633 B2 | 1/2011 | Bekele et al. | |
| 8,586,013 B2 | 11/2013 | Bradshaw et al. | |
| 8,637,057 B2 | 1/2014 | Patel et al. | |
| 9,320,689 B2 | 4/2016 | Cassin et al. | |
| 10,369,387 B2 | 8/2019 | El-Khouri et al. | |
| 2004/0126350 A1 | 7/2004 | Blin et al. | |
| 2006/0115439 A1 | 6/2006 | Lu | |
| 2006/0292096 A1 | 12/2006 | Yu | |
| 2007/0093619 A1 | 4/2007 | Bui et al. | |
| 2009/0074702 A1 | 3/2009 | Allard et al. | |
| 2011/0117043 A1 * | 5/2011 | Dempsey | A61Q 1/10 424/70.7 |
| 2011/0293550 A1 | 12/2011 | Bui et al. | |
| 2012/0301415 A1 | 11/2012 | Bui et al. | |
| 2015/0174048 A1 | 6/2015 | Tachon et al. | |
| 2017/0021518 A1 | 1/2017 | Hsu | |
| 2017/0281478 A1 | 10/2017 | El-Khouri | |
| 2017/0281519 A1 | 10/2017 | El-Khouri | |
| 2017/0281520 A1 | 10/2017 | El-Khouri | |
| 2017/0281521 A1 | 10/2017 | El-Khouri | |
| 2018/0177711 A1 | 6/2018 | El-Khouri | |
| 2018/0214370 A1 * | 8/2018 | El-Khouri | A61K 8/927 |
| 2018/0243202 A1 | 8/2018 | El-Khouri | |
| 2019/0262257 A1 * | 8/2019 | Rosario-Melendez | A61K 8/31 |

FOREIGN PATENT DOCUMENTS

| | | |
|---|---|---|
| FR | 2 918 273 A1 | 1/2009 |
| FR | 2 931 673 A1 | 12/2009 |
| FR | 2 967 910 A1 | 6/2012 |
| WO | 2005/100444 A1 | 10/2005 |

OTHER PUBLICATIONS

French Search Report dated May 5, 2021 in French Patent Application No. 2008405 (with English translation of Category of Cited Documents), 9 pages.

* cited by examiner

*Primary Examiner* — Jyothsna A Venkat
(74) *Attorney, Agent, or Firm* — Oblon, McClelland, Maier & Neustadt, L.L.P.

(57) ABSTRACT

A cosmetic system including a lip basecoat composition that includes at least one first silicone film-forming agent, colorant, and a volatile hydrocarbon oil, and a topcoat composition including at least one second silicone film-forming agent in a non-volatile oil carrier. Methods and topcoats are also provided.

1 Claim, No Drawings

LONG WEAR LIP COSMETIC SYSTEM AND TOPCOAT

FIELD OF THE INVENTION

The present invention relates to a topcoat composition for long-wear lip compositions comprising at least one silicone film-forming agent, as well as to cosmetic systems, kits and methods of treating, making-up and enhancing the appearance of lips, including a topcoat composition for application to a basecoat composition.

DISCUSSION OF THE BACKGROUND

Many cosmetic compositions, including pigmented cosmetics such as lipsticks or lip colors, have been formulated in an attempt to possess long-wearing properties upon application. Unfortunately, many of these compositions do not generally possess both good long-wear/transfer-resistance properties as well as high gloss.

For example, with respect to lip compositions, commercial products containing silicon resins such as MQ resins are known. Such products are known to provide good long wear properties/transfer-resistance.

At times, a second composition (topcoat) is separately applied to such products to improve poor properties of the compositions to make the products acceptable to consumers. However, topcoat compositions tend to decrease the long-wear/transfer-resistance properties of the lip compositions, thereby rendering the long-wear/transfer resistant composition less acceptable to consumers and less acceptable for their intended purpose.

Thus, there remains a need for improved lip compositions and systems having improved cosmetic properties, particularly good transfer-resistance, feel and shine characteristics upon application.

Accordingly, one aspect of the present invention is a topcoat composition for long-wear lip compositions which provide or maintain good cosmetic properties such as, for example, good transfer-resistance, feel and shine properties upon application to a long-wear lip composition.

SUMMARY OF THE INVENTION

In one aspect, the present invention relates to a cosmetic system comprising (1) a lip basecoat composition including at least one first silicone film-forming agent, colorant, and a volatile hydrocarbon oil, and (2) a topcoat composition including at least one second silicone film-forming agent in a non-volatile oil carrier.

In another aspect, the present invention relates to a method of making up the lips. The method includes applying to the lips a first composition including at least one first silicone film-forming agent, colorant, and a volatile hydrocarbon oil to form a basecoat. After a waiting period, a second composition including at least one second silicone film-forming agent in a non-volatile oil carrier is applied to form a topcoat over the basecoat.

In another aspect, the present invention relates to a topcoat composition for use on the lips, wherein the topcoat consists essentially of from about 15% by weight to about 30% by weight of at least one silicone film-forming agent; from about 60% to about 85% of a non-volatile silicone oil; and from about 0.001% to about 10% by weight of one or more cosmetic additives, wherein the at least one silicone film-forming agent and the one or more cosmetic additives are dispersed or dissolved in the non-volatile silicone oil.

DETAILED DESCRIPTION OF THE INVENTION

According to the invention, the term "anhydrous" refers to a composition not containing any water, that is to say a composition in which the water that may be present comes only from the water of crystallization or of adsorption of the starting materials. In any case contains less than about 2% by weight of water, such as less about 1% water, such as less than about 0.5% water such as less about 0.1% of water.

All percentages of ingredients herein are listed on an actives basis unless specifically stated otherwise. Further, all percentages of ingredients are percent by weight unless specifically stated otherwise.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 15%, such as within 10%, of the indicated number. For example, about 10% means from 8.5% to 11.5%, such as between 9% and 11%.

"Film former" or "film forming agent" or "film forming polymer" or "film forming resin" as used herein mean a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Liquid" or "liquid cosmetic" or "liquid lipstick" or "liquid composition" means a composition having a fixed volume, flows to cover the bottom and assumes the shape of the portion of the container it fills and is slightly compressible.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion and the one far along described.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphategroups, siloxane groups, and polysiloxane groups. The substituent(s) may be further substituted.

"Substantially free" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. In certain embodiments, substantially free means less than about 2% of the identified ingredient, such as less than about 1%, such as less than about 0.5% of the ingredient.

"About," as referring to, for example, concentrations of ingredients, means within 10% to 15% of the indicated number.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

All concentrations in this specification are by weight unless otherwise specifically stated differently.

"Keratinous materials" includes materials containing keratin such as hair, skin, eyebrows, lips and nails.

"Volatile", as used herein, means having a flash point of less than about 100° C.

"Non-volatile", as used herein, means having a flash point of greater than about 100° C.

"Actives basis" as used herein means considering only the particular component of ingredient (e.g., in a composition) and ignoring other chemically unrelated components that may be also be present in the same raw material source of that particular component.

The compositions and methods of the present invention can comprise, consist of, or consist essentially of the essential elements and limitations of the invention described herein, as well as any additional or optional ingredients, components, or limitations described herein or otherwise useful.

Basecoat Composition

According to embodiments of the present invention, a long-wear lip composition including at least one silicone film-forming agent is provided. Preferably, the silicone film-forming agent is selected from the group consisting of silicone resins, polyorganosiloxane copolymers, and mixtures thereof. The basecoat compositions of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, include an external or continuous fatty phase. The composition can also be a molded composition or cast as a stick or a dish.

In certain notable embodiments, the basecoat is a liquid. In certain other notable embodiments, the basecoat is a solution or dispersion including at least one silicone film-forming agent and at least one colorant in a volatile hydrocarbon oil.

Silicone Resins

According to preferred embodiments, the long-wear lip compositions of the present invention include at least one silicone resin. Examples of suitable silicone resins include those described, for example, in U.S. Pat. Nos. 5,505,937, 5,911,974, 5,965,112, 5,985,298, 6,074,654, 6,780,422, 6,908,621, the disclosures of which are hereby incorporated by reference in their entirety.

According to preferred embodiments, the long-wear lip compositions contain siloxysilicate resins. One non-limiting example of a siloxysilicate in accordance with the present invention is trimethylsiloxysilicate, which may be represented by the following formula:

$[(CH_3)_3SiO]_x(SiO_{4/2})_y$ wherein x and y may, for example, range from 50 to 80. Such siloxysilicates are commercially available from General Electric, Dow Corning, Wacker, Milliken, Siltech, Grant Industries, Momentive and Shin-Etsu Silicones under the tradename Resin MQ®.

According to preferred embodiments, the long-wear lip compositions contain silsesquioxane resins such as, for example, polypropyl silsesquioxane resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film-forming resin is made up predominantly of tri-functional units (or T units), it is generally called a silsesquioxane resin, which is described, for example in US 2006/0292096, herein incorporated by reference in its entirety.

Examples of silsesquioxane resins that may be used in the present invention are alkyl silsesquioxane resins that are silsesquioxane homopolymers and/or copolymers having an average siloxane unit of the general formula $R^1{}_n SiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer includes $R^1SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference in their entirety.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer includes $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

According to preferred embodiments, the long-wear lip composition contains at least one silicone resin selected from the group consisting of siloxysilicate resins, silsesquioxane resins, and mixtures thereof.

The at least one silicone resin is preferably present in the long-wear lip compositions of the present invention in an amount ranging from about 5% to about 30% by weight, preferably from about 10% to about 25% by weight, and preferably from about 15% to about 20% by weight, including all ranges and subranges therebetween, all weights being based on the weight of the composition as a whole.

Volatile Hydrocarbon Oils

The basecoat composition includes at least one volatile hydrocarbon oil. The term "oil," as used herein, means nonaqueous compounds having a melting point of less than about 25° C. and at atmospheric pressure (1.013×.$10^5$ Pa). Oils are generally immiscible with water wherein "immiscible" is intended to mean that the mixing of the same amount of water and oil, after mixing (for example Rayneri 550 rpm; 10 minutes), does not result in a stable solution including just one phase, under normal temperature and pressure conditions Oils generally include a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties. In certain embodiments, the oil is not surface active—i.e., when added in a weight concentration of 1% to water does not reduce surface tension of the water to less than 50 dynes/cm.

Examples of suitable volatile hydrocarbon oils include, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

In addition to the volatile hydrocarbon oil, the basecoat may optionally include one or more volatile silicone oils. The volatile silicone oil, if present, may be chosen from linear or cyclic silicone oils, such as those having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

According to certain embodiments the one or more volatile hydrocarbon oils are present in a concentration by weight greater that is greater than the concentration by weight of the one or more volatile silicone oils. According to certain other embodiments the one or more volatile hydrocarbon oils are present in a concentration by weight that is at least 2 to about 10 times that of the one or more volatile silicone oils.

The at least one volatile hydrocarbon oil is generally present in the compositions of the present invention in an amount ranging from about 5% to about 50% by weight; such as from about 10% to about 45% by weight; such as from about 15% to about 40% by weight, all weights being based on the weight of the composition as a whole.

The at least one volatile silicone oil if present, is generally present in the compositions of the present invention in an amount ranging from about 1% to about 25% by weight; such as from about 2% to about 15% by weight; such as from about 3% to about 10% by weight, all weights being based on the weight of the composition as a whole.

According to notable embodiments, the basecoat compositions of the present invention may include at least one polyorganosiloxane copolymer. The polyorganosiloxane copolymer useful herein is preferably a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions. Non-limiting examples of polyorganosiloxane copolymers are disclosed, for example in U.S. Pat. No. 8,945,525, the disclosure of which is hereby incorporated by reference in its entirety.

Additional polyorganosiloxane copolymers which may be used in the long-wear lip compositions of the present invention include those described in documents U.S. Pat. No. 5,874,069, U.S. Pat. Nos. 5,919,441, 6,051,216, and 5,981,680, the entire contents of which are hereby incorporated by reference in their entirety.

A preferred polyorganosiloxane copolymer for use in the present invention contain at least one moiety chosen from formula (III):

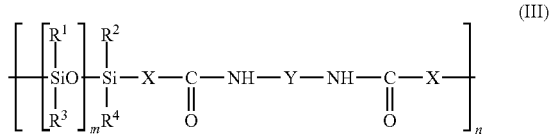

and formula (IV)

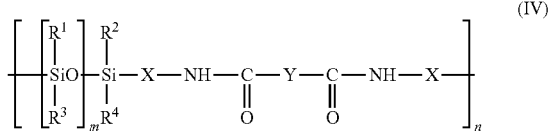

in which:
(a) $R^1$, $R^2$, $R^3$ and $R^4$ are the same or different and may be selected from the group consisting of methyl, ethyl, propyl, isopropyl, a siloxane chain, and phenyl;
(b) X is a linear or branched chain alkylene having 1-30 carbons;
(c) Y is selected from the group consisting of linear or branched chain alkylenes having 1-40 carbons;
(d) m is a number between 1 and 700;
(e) n is a number between 1 and 500.

Particularly preferred polyorganosiloxane copolymers useful herein are commercially available from Dow Corning under the tradenames DC 8178® and DC 8179®, which are known under the INCI denomination of Nylon-611/Dimethicone Copolymer.

Preferably, the polyorganosiloxane copolymer is present in the long-wear lip compositions of the present invention in an amount ranging from about 2% to about 35% by weight, preferably from about 5% to about 30% by weight, and preferably from about 7% to about 20% by weight, including all ranges and subranges therebetween, all weights being based on the weight of the composition as a whole.

According to preferred embodiments, the long-wear lip composition may further include as least one silicone elastomer. Preferably, the silicone elastomer is a non-emulsifying silicon elastomer. "Non-emulsifying" defines organopolysiloxane elastomers that do not contain hydrophilic chains, in particular polyoxyalkylene (especially polyoxyethylene or polyoxypropylene) or polyglyceryl units. Thus, according to one particular embodiment of the invention, the composition includes a silicone elastomer that is free of polyoxyalkylene units and polyglyceryl units.

Suitable examples of non-emulsifying elastomers are described in U.S. Pat. No. 8,637,057, the disclosure of which is hereby incorporated by reference in its entirety.

Further suitable examples of non-emulsifying elastomers useful in this invention include but not limit those sold under the names KSG-6, KSG-15, KSG-16, KSG-18, KSG-41, KSG-42, KSG-43 and KSG-44 by the company Shin-Etsu, DC 9040, DC 9041, DC 9509, DC 9505 and DC 9506, by the company Dow Corning, and SFE 839 by the company Momentive Performance Materials.

The silicone elastomers are preferably in the form of a gel or a powder.

According to preferred embodiments, the silicone elastomer particles are conveyed in the form of a gel formed from an elastomeric organopolysiloxane included in at least one hydrocarbon-based oil and/or one silicone oil. In these gels, the organopolysiloxane particles are often non-spherical particles. Not limiting examples of silicone elastomers useful in this invention are dimethicone crosspolymer gels (blends of dimethicone crosspolymers in solvents) having viscosity values from about 150 and to about 700 mm²/s, from about 200 to about 650 mm²/s and from about 300 to about 600 mm²/s, including all ranges and subranges therebetween.

Particularly useful for this invention may be blends of high molecular weight silicone elastomers in volatile solvents, such as silicone oils, hydrocarbon oils and mixtures thereof.

Specific examples of suitable silicone elastomeric gels include DC EL-8040 ID (INCI name: Isododecane (and) Dimethicone Crosspolymer) and DC EL-9140 DM (INCI name: Dimethicone (and) Dimethicone Crosspolymer), supplied by Dow Corning.

Non-limiting examples of silicone elastomers and their synthesis are disclosed, for example in U.S. Pat. No. 8,637,057 and US/20150174048, both of which are herein incorporated by reference in their entirety.

Although not wishing to be bound by any particular theory, it is believed that the silicone elastomer thickens the composition, adds the cushiony (spongy) effect and/or improves the application properties of the long-wear lip composition. Also, it provides a very soft feel and/or mattifying effect after application.

Preferably, the silicone elastomer is present in a content ranging from 1 percent to 30 percent by weight of active material (dry matter), preferably from about 1.5 percent to about 20 percent, and preferably from 2 percent to 10 percent by weight relative to the total weight of the long-wear lip composition, including all ranges and subranges therebetween.

Further, basecoat compositions of the present invention may optionally further include at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 15%, from about 1.5% to about 12%, and from about 2% to about 10%, based on the weight of the composition.

The basecoat compositions of the present invention may optionally further include at least one filler. Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (hectorite, bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

The basecoat compositions of the present invention may optionally further include at least one silica aerogel. Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. Silica aerogels, in general, have been disclosed in U.S. Pat. No. 9,320,689, the entire content of which is hereby incorporated by reference.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references AEROGEL TLD 201, AEROGEL OGD 201, AEROGEL TLD 203, ENOVA® AEROGEL MT 1100, ENOVA AEROGEL MT 1200.

In particular, the aerogel sold under the name VM-2270 (INCI name: Silica silylate), by the company Dow Corning, the particles of which have a mean size ranging from 5-15 microns and a specific surface area per unit of mass ranging from 600 to 800 $m^2/g$ can be used.

The silica aerogel particles can be used in the inventive compositions from 0.1% to about 8% by weight, preferably from 0.25% to 6% by weight, and preferably from 0.5% to 4% by weight, including all ranges and subranges therebetween, all weights based on the weight of the composition as a whole.

According to preferred embodiments, the basecoat composition of the present invention may include at least one wax. For the purposes of the present invention, a wax is a lipophilic fatty compound (similar to those described above for "oil") except that it is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes can generally be those used in cosmetics. The waxes may be of natural origin, for instance beeswax, carnauba wax, candelilla wax, ouricoury wax, Japan wax, cork fiber wax, sugar cane wax, paraffin wax, lignite wax, microcrystalline waxes, lanolin wax, montan wax, ozokerites and hydrogenated oils, for instance hydrogenated jojoba oil.

The waxes also may be of synthetic origin, for instance polyethylene waxes derived from the polymerization of ethylene, waxes obtained by Fischer-Tropsch synthesis, esters of fatty acids and of glycerides that are solid at 40° C.

Particular waxes include, for example, polyethylene waxes, for example the product sold under the name Performalene 500-L Polyethylene (New Phase Technology), and polymethylene waxes, for instance the product sold under the name Cirebelle 303 (Sasol).

Particular waxes include, for example, silicone waxes such as polypropylsilsesquioxane wax substituted with alkyl units having at least 30 carbons. Polypropylsilsesquioxane waxes, in general, have been disclosed in patent publication WO2005/100444 and U.S. Pat. No. 8,586,013, the entire contents of which are hereby incorporated by reference in their entirety. A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax.

The basecoat compositions of the present invention may optionally further include at least one cosmetically or dermatologically acceptable additional additive such as thickener, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

According to certain embodiments, basecoat compositions of the present invention may include from about volatile hydrocarbon oil in a concentration by weight from about 20%, 30% or 40% to about 65%, 75%, or 85%; at least one silicone resin in a concentration by weight from about 5%, 10% or 15% to about 25%, 35%, or 45%; colorant in a concentration by weight from about 1%, 2% or 5% to about 5%, 10% or 20%; and optionally a filler in a concentration by weight from about 2%, 3% or 5% to about 6%, 10%, or 20%. In certain of these embodiments, the basecoat is substantially free of one or more of: silicone oils, water, waxes, and non-volatile hydrocarbon oils.

Topcoat Composition

According to the present invention, topcoat compositions including at least one film-forming agent and non-volatile oil carrier are provided. According to certain embodiments, the topcoat composition consists essentially of at least one silicone resin and at least one non-volatile oil, such as a non-volatile silicone oil. Preferably, when the topcoat composition is applied to a long-wear lip composition such as the basecoats described herein, the topcoat composition does not inhibit the transfer-resistance of the long-wear lip composition.

Silicone resins useful in the topcoat are those described above with reference to the basecoat. However, the basecoat and topcoat need not include any or all of the same silicone resins. According to certain embodiments, the silicone resin is selected from the group consisting of siloxysilicate resins, silsesquioxane resins, and mixtures thereof. In certain embodiments, the silicone resin includes or consists of siloxysilicate resins such as trimethylsiloxysilicate.

The concentration by weight of the one or more silicone resins in the topcoat may be from at least about 10%, such as at least above 15%. According to certain embodiments, the concentration by weight of the one or more silicone resins ranges from about 15% or 20% to about 25% or 30% by weight.

Non-Volatile Carrier

The non-volatile oil carrier includes, consists essentially of or consists of one or more non-volatile oils. The terms "oil" and "non-volatile" are as described above. According to certain embodiments, the non-volatile oil has a vapor pressure at 25° C. and atmospheric pressure that is non-zero and is less than 0.02 mmHg (2.66 Pa) and better still less than $10^{-3}$ mmHg (0.13 Pa).

The non-volatile oil carrier may include relatively small concentrations of volatile oils, such as volatile silicone oils. In certain embodiments, the concentration of volatile oils in the topcoat is less than the concentration of the non-volatile oils. For example, the nonvolatile oil carrier may have up to 40%, such as up to 30%, such as up to 20%, such as up to 10%, such as up to 5%, such as up to 1% of volatile oils, measured on a concentration by weight basis versus the total oil in the non-volatile oil carrier.

According to a particular embodiment of the present invention, the non-volatile oil is a high viscosity oil which is a silicone oil and/or a hydrocarbon oil. "High viscosity" means an oil having a viscosity greater than 100 cSt, particularly greater than 250 cSt at 25° C. Most particularly, the non-volatile oil is selected from a silicone oil. Such oils are described, for example in US 2011/0293550 and US 2004/0126350, both of which are herein incorporated by reference.

In particular, the non-volatile silicone oils that may be used in the invention preferably have a viscosity at 25° C. between 9 cSt and 800 000 cSt, preferably less than or equal to 600 000 cSt and preferably less than or equal to 500 000 cSt. The viscosity of these silicone oils may be measured according to standard ASTM D-445.

According to certain embodiments, the non-volatile silicone oil is a non-phenylated silicone oil. The expression "non phenylated silicone oil" or "non phenylated silicone oil" means a silicon oil having no phenyl substituent.

According to one embodiment, a composition according to the invention contains at least one non-phenylated linear silicone oil. Representative examples of these non-volatile non phenylated silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") including alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C.

Specific examples of suitable for this invention high viscosity silicone oils include, but are not limited to, Xiameter® silicone fluids from Dow Corning.

The at least one non-volatile silicone oil, if present, is preferably present in the compositions of the present invention in an amount ranging from about 2% to about 30% by weight, including from about 4% to about 25% by weight, typically about 6% to about 20% by weight, based on the total weight of the composition, including all ranges and subranges within these ranges.

The non-volatile non phenylated silicon oil is preferably chosen from dimethicone oils, preferably chosen from polydimethylsiloxanes (PDMS); alkyl dimethicones.

"Dimethicone" (INCI Name) corresponds to polydimethylsiloxane (chemical name).

The PDMSs may include alkyl or alkoxy groups, which are pendent and/or at the end of the silicone chain, these groups each containing from 2 to 24 carbon atoms, such as cetyldimethicone sold under the commercial reference ABIL WAX 9801 from Evonik Goldschmidt, The PDMS may include aliphatic and/or aromatic groups, or functional groups such as hydroxyl, thiol and/or amine groups, polyalkylmethylsiloxanes such as cetyldimethicone sold under the commercial reference ABIL WAX 9801 from Evonik Goldschmidt, or polyalkylmethylsiloxane optionally substituted with a fluorinated group, such as polymemyltrifluoropropyldimethylsiloxanes, The non-phenylated linear silicone oil may be chosen especially from the silicones of formula (I):

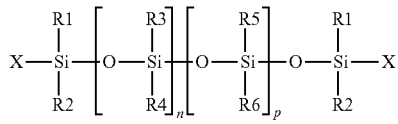

in which: R groups are together or separately, an alkyl radical containing 1 to 6 carbon atoms, vinyl radical, an amine radical or a hydroxyl radical, X is an alkyl radical containing from 1 to 6 carbon atoms, a hydroxyl radical or an amine radical, n and p are integers chosen so as to have a fluid compound, in particular whose viscosity at 25° C. is between 9 centistokes (cSt) (9×10 W/s) and 800 000 cSt.

According to a particular embodiment, the non-volatile silicone oil includes, consists essentially of or consists of polydimethylsiloxanes having a viscosity from about 100 cSt to about 5000 cSt.

According to other embodiments, the non-volatile silicone oil includes at least one non-volatile phenylated silicone oil.

The expression "phenylated silicone oil" or "phenyl silicone oil" means a silicone oil having at least one phenyl substituent.

Such a phenyl silicone oil is preferably trimethyl pentaphenyl trisiloxane, or Tetramethyl Tetraphenyl Trisiloxane. Such oils are especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane), or Tetramethyl Tetraphenyl Trisiloxane sold under he reference Dow Corning 554 Cosmetic Fluid by Dow Corning may also be used. d) the phenyl silicone oils corresponding to the following formula (TV):

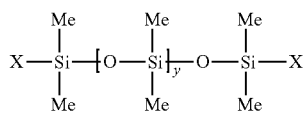

in which Me represents methyl, y is between 1 and 1,000 and X represents —CH2-CH(CH$_3$)(Ph). e) the phenyl silicone oils corresponding to formula (V) below:

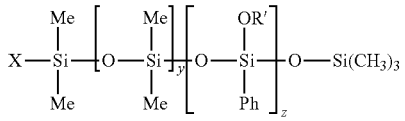

in which Me is methyl and Ph is phenyl, OR' represents a group —OSiMe$_3$ and y is 0 or ranges between 1 and 1000, and z ranges between 1 and 1000. In particular, y and z are such that compound (V) is a non-volatile oil.

As preferred non-volatile silicone oils, examples that may be mentioned include phenyl trimethicones, Tetramethyl Tetraphenyl Trisiloxane, diphenylsiloxyphenyltrimethicone, diphenylsiloxyphenyldimethicone, trimethylpentaphenyl trisiloxane, phenyldimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

In certain embodiments, the topcoat includes from about 15% by weight to about 30% by weight of the second silicone film-forming agent and from about 60% to about 85% by weight of one or more non-volatile silicone oils.

Additional Ingredients

According to certain embodiments, the topcoat composition may include additional ingredients such as preservatives, natural extracts, colorants, waxes, polymers vitamins, antioxidants, skin benefit agents, and the like. The concentrations of these other ingredients may be, for examples, less than about 20%, such as less than about 10%, such as less than about 5% by weight. According to certain embodiments the topcoat composition includes from about 0.001%, 0.005% or 0.1% to about 0.5%, 1%, 2%, 5% or 10% of a cosmetic additive, such as an additive selected from a group consisting of vitamins, antioxidants, natural extracts, polymers, or colorants.

According to certain other embodiments, the topcoat composition is substantially free of one or more or even all of: non-volatile hydrocarbon oils, volatile oils, waxes, colorants, C2-C4 monoalcohols, glycols, and water. According to certain other embodiments the topcoat composition is substantially free of diglyceryl polyacyladipate and/or non-volatile phenylated silicone oils. According to certain other embodiments the topcoat composition is substantially free of colorants.

According to certain other embodiments, the topcoat composition for use on the lips consists essentially of from about 15% by weight to about 30% by weight of at least one silicone film-forming agent; from about 65% to about 85% of a non-volatile silicone oil; and from about 0.001% to about 10% by weight of one or more cosmetic additives, wherein the at least one silicone film-forming agent and the one or more cosmetic additives are dispersed or dissolved in the non-volatile silicone oil. The topcoat may be substantially free of one or more of: colorants, hydrocarbon oils, water, waxes, and phenylated silicone oils, diglyceryl polyacyladipate, and/or volatile oils.

According to preferred embodiments, the basecoat and topcoat are included in a cosmetic system or "kit." Accordingly, in certain embodiments, the kit includes (1) a long-wear lip composition including at least one silicone film-forming agent, colorant, and a volatile hydrocarbon oil; and (2) a topcoat composition including at least one second silicone film-forming agent in a non-volatile oil carrier.

According to preferred embodiments, methods for enhancing the appearance of lips including applying a long-wear lip composition including at least one silicone film-forming agent, colorant, and a volatile hydrocarbon oil to the lips to form a basecoat, and after some waiting period such as sufficient to dry the basecoat or to allow a sufficient amount of volatile oil to evaporate; (2) applying a (topcoat) composition including at least one second silicone film-forming agent in a non-volatile oil carrier to form a topcoat over the basecoat, are provided.

Preferably, when the topcoat composition is applied to the long-wear lip composition, the topcoat composition does not inhibit the transfer-resistance of the long-wear lip composition.

The compositions and methods of the present invention can "comprise," "consist of" or "consist essentially of" the identified ingredients and process steps. For purposes of the compositions and methods of the present invention where the invention "consists essentially of" the identified ingredients and/or process steps, the sole "basic and novel property" of such compositions and/or methods is transfer-resistance. Further, given that it is contemplated that other transfer-resistance enhancers or boosters (for example, additional film-forming agents) can be added to the invention methods and compositions in the context of the present invention, a "material effect" on the basic and novel property of the invention can only be an adverse effect. That is, because positive effects on transfer-resistance properties (such as those effected by additional film-forming agents) are within the scope of the present invention, only ingredients which have a material adverse effect on transfer-resistance properties would be relevant to determining whether or not compositions or methods "consist essentially of" the required elements.

Without wishing to be held by theory, Applicants believe that the inventive cosmetic system is surprisingly able to provide long lasting wear and long lasting high gloss due to the selection of ingredients. It is believed that the volatile hydrocarbon oil of the basecoat evaporates quickly allowing the basecoat film-forming agent to set. The non-volatile silicone in the topcoat simultaneously plasticizes the silicone film formers in the basecoat and the topcoat and builds durable gloss without disrupting the basecoat layer underneath.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The present invention will be better understood from the examples which follow. The examples are intended to be nonrestrictive and explanatory only, with the scope of the invention defined by the claims.

Example 1—Invention Compositions

The following tables set forth a basecoat and topcoat that are consistent with embodiments of the present invention.

| Ingredient (% by Weight) | Basecoat | Topcoat |
|---|---|---|
| Isododecane | 50-60 | |
| Triethylsiloxysilicate | 15-25 | 15-25 |
| Dimethicone, 1000 cSt | — | 75-85 |
| Nylon-611/Dimethicone Polymer | 5-15 | |
| Colorants | 3-8 | |
| Fillers | 6-10 | |
| Additional Ingredients | 0-5 | 0-0.1 |

Example 2—Exemplary Method of Preparing Invention Composition(s)

The basecoat composition is made by conventional techniques, for example, by: by charging the vessel with optional filler at room temperature and homogenizing, adding pigments (colorants), homogenizing, adding copolymer such as Nylon-611/Dimethicone Polymer, homogenizing and applying vacuum, adding silicone resin and isododecane at elevated temperature such as 80 C, homogenizing, adding additional fillers, homogenizing, and allowing to cool.

The topocat composition is made by charging a vessel with dimethicone, adding vitamin E (additional ingredient) under vortex shear; slowly adding triethylsiloxysilicate, increasing mixing speed and allow to mix while maintaining temperature below 35° C. until Triethylsiloxysilicate is well-dispersed.

Example 3—Wear Testing

A basecoat and topcoat consistent with Example 1 were tested together as a cosmetic system. One hundred and thirty-four women applied the basecoat and topcoat in a manner consistent with the invention described herein.

After wearing the cosmetic system, the women were asked whether the product lasted sixteen hours (yes or no). One hundred seven (80%) of the women answered yes. This is surprisingly high, especially for a glossy product.

The invention claimed is:
1. A top coat composition for lips, wherein the top coat composition for lips consists of:
    from about 15% by weight to about 30% by weight of trimethylsiloxysilicate resin;
    from about 60% to about 85% of polydimethylsiloxane; and
    from about 0.001% to about 10% by weight of one or more cosmetic additives, wherein the trimethylsiloxysilicate and the one or more cosmetic additives are dispersed or dissolved in the polydimethylsiloxane wherein the top coat composition for lips is free of colorants.

* * * * *